(12) United States Patent
Schoonover

(10) Patent No.: US 11,383,016 B2
(45) Date of Patent: Jul. 12, 2022

(54) CUSTOM DATA FIELDS FOR AUTOMATED APHERESIS PROCEDURES

(71) Applicant: Fenwal, Inc., Lake Zurich, IL (US)

(72) Inventor: Matthew J. Schoonover, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 535 days.

(21) Appl. No.: 16/254,826

(22) Filed: Jan. 23, 2019

(65) Prior Publication Data
US 2019/0247565 A1    Aug. 15, 2019

Related U.S. Application Data

(60) Provisional application No. 62/628,657, filed on Feb. 9, 2018.

(51) Int. Cl.
*A61M 1/38* (2006.01)
*A61B 5/15* (2006.01)
(Continued)

(52) U.S. Cl.
CPC ......... *A61M 1/38* (2013.01); *A61B 5/150786* (2013.01); *A61B 5/7485* (2013.01);
(Continued)

(58) Field of Classification Search
CPC .............. A61M 1/3496; A61M 1/3612; A61M 1/3672; A61M 1/38; A61M 2202/0429;
(Continued)

(56) References Cited

U.S. PATENT DOCUMENTS

| | | | | |
|---|---|---|---|---|
| 2003/0093503 | A1* | 5/2003 | Yamaki | G16H 40/63 709/220 |
| 2014/0069868 | A1* | 3/2014 | Nguyen | A61M 1/3643 210/650 |
| 2015/0115180 | A1* | 4/2015 | Schoonover | A61M 1/3455 250/565 |

FOREIGN PATENT DOCUMENTS

WO    WO01/65463 A2    9/2001

OTHER PUBLICATIONS

Ezzelle, J. et al., Guidelines on Good Clinical Laboratory Practice; Bridging Operations between Research and Clinical Research Laboratories, Journal of Pharmaceutical and Biomedical Analysis, pp. 18-29, (Jan. 7, 2008).

(Continued)

*Primary Examiner* — John Kim
(74) *Attorney, Agent, or Firm* — Cool Alex Ltd.

(57) ABSTRACT

A method and automated system for processing blood in which the automated system includes a programmable controller, a database, and an interactive display screen for displaying information and receiving operator input. The programmable controller is configured to automatically control the system to perform the method. Upon activation of the system, the screen displays a listing of different blood processing procedures that may be performed using the system. The operator may then input into the controller an identification of a specified blood processing procedure that is to be performed, such that an initial list of parameters that are associated with the specified blood processing procedure are displayed on the screen. The operator may then input into the controller an identification of the parameters that are to populate the display screen during performance of the procedure and indicate a format in which the selected parameters are to be presented on the display screen. The controller then creates a display for the specified blood (Continued)

processing procedure. Current values of the selected parameters in the selected format are displayed on the screen during performance of the specified procedure. The controller automatically saves an image of the display screen periodically during performance of the specified blood processing procedure, and transfers information from the saved images of the display screens to a procedure record form.

20 Claims, 6 Drawing Sheets

(51) Int. Cl.
  *A61B 5/00* (2006.01)
  *A61M 1/34* (2006.01)
  *A61M 1/36* (2006.01)
  *G16H 20/40* (2018.01)
  *G16H 30/40* (2018.01)
  *G16H 40/63* (2018.01)
(52) U.S. Cl.
  CPC ........ *A61M 1/3496* (2013.01); *A61M 1/3612* (2014.02); *A61M 1/3672* (2013.01); *G16H 20/40* (2018.01); *G16H 30/40* (2018.01); *G16H 40/63* (2018.01); *A61M 2202/0429* (2013.01); *A61M 2205/505* (2013.01); *A61M 2205/6072* (2013.01); *G05B 2219/36371* (2013.01)
(58) Field of Classification Search
  CPC .... A61M 2205/505; A61M 2205/6072; A61B 5/7485; A61B 5/150786; G16H 20/40; G16H 30/40; G16H 40/63; G05B 2219/36371
  See application file for complete search history.

(56) References Cited

OTHER PUBLICATIONS

Kishore, Aseem, Capture Screenshots at Defined Time Intervals Automatically in Windows, Retrieved from the Internet: https://www,online-tech-tips.com/free-software-downloads/capture-screenshots-at-defined-time-intervals-automatically/, pp. 1-13 (May 26, 2016).

European Patent Office, extended European Search Report, counterpart EP Appl. No. 19153269.6, 9 pages, (dated Jul. 8, 2019).

* cited by examiner

FIG. 5

RBC Exchange Procedure Data Settings

| | | | | | |
|---|---|---|---|---|---|
| 9 | Procedure Start Time | | AC Used | 12 | RF to Patient |
| 10 | Procedure End Time | 5 | AC to Patient | 14 | Plasma Returned |
| 8 | Procedure Time | | ACWB Processed | 13 | Removed Volume |
| 4 | FCR | 11 | WB Processed | 7 | Fluid Balance (mL) |
| 3 | End Hct | | RBC RF to Patient | | Fluid Balance (%) |
| 1 | Starting Hct | | Saline RF to Patient | | Saline Used |
| 2 | Depletion Hct | | Albumin RF to Patient | 6 | Saline to Patient |

FIG. 6

Procedure Results

| | | | |
|---|---|---|---|
| Starting Hct | 35% | Procedure Time | 75 min |
| Depletion Hct | 30% | Procedure Start Time | 10:40 AM |
| End Hct | 35% | Procedure End Time | 11:55 AM |
| FCR | 33% | WB Processed | 12:00 mL |
| AC to Patient | 179 mL | RF to Patient | 1513 mL |
| Saline to Patient | 55 mL | Removed Volume | 1755 mL |
| Fluid Balance (mL) | 43 mL | Plasma Returned | 1326 mL |

CUSTOM DATA FIELDS FOR AUTOMATED APHERESIS PROCEDURES

FIELD OF THE DISCLOSURE

The present application is directed to systems and methods for processing blood or blood products, and more particularly to systems and methods for processing blood or blood products using an automated system having a programmable controller with an interactive display screen for displaying information and receiving operator input.

BACKGROUND

A representative automated system for processing blood and blood products may be seen with reference to U.S. Patent Application Publication No. 2016/0175509. While the system described and illustrated therein is for performing plasmapheresis, the systems and methods described herein for selecting the information to be presented on the display screen may be used with virtually any automated apheresis system, including without limitation those configured to perform red blood cell collection, therapeutic plasma exchange; red blood cell exchange, cell washing, and the like.

In the system disclosed in U.S. Patent Application Publication No. 2016/0175509, a disposable set is used to collect virtually cell-free plasma by means of a rapidly rotating separator (membrane filter) to separate whole blood into plasma for collection and concentrated cells for reinfusion to the donor.

A donor is connected to the system throughout the procedure, with a single venipuncture site and a single apheresis needle used to perform sequential cycles of alternating collection and reinfusion phases. During the collection phase, blood is drawn from the donor and plasma is separated and collected. The separated (concentrated) cells are pumped into a reservoir and, during the return phase, reinfused to the donor using the same venipuncture site and apheresis needle.

The system includes a touch screen that enables the operator to control the procedure, gather status information and handle error conditions. More particularly, the touch screen displays information and prompts the operator to perform different actions. Different displays are shown on the screen at various stages of the procedure being performed, including pre-procedure estimates, intra-procedure variables, and post procedure summaries and results. Preferably the controller is configured to permit the operator to save, or to automatically save, the screen displays for the various stages of the procedure so that the information may be later retrieved, reviewed and/or transferred to a procedure record form or database.

The format of the displays, that is, the information selected to be displayed and the arrangement of the information is typically established by the manufacturer of the system and pre-programmed into the programmable controller. Typically, the system operator has little or no ability to modify the displays to meet his or her particular needs. For example, some of the data displayed may not be needed by some operators. Further, the order in which the information is displayed on the screen may not match that in the record of the procedure that is prepared by the operator, which could lead to entry errors when transferring the information to the record of the procedure. Thus, there is a need for system operators to be able to customize the display of the systems to meet their particular needs and preferences.

SUMMARY

In a first aspect, a method is provided for processing blood or blood products using an automated system including a programmable controller, a database, and an interactive display screen for displaying information and receiving operator input. The method comprises the steps of, upon activation of the system, displaying on the screen a listing of different blood processing procedures that may be performed using the system; upon inputting into the controller an identification of a specified blood processing procedure that is to be performed, displaying on the screen an initial list of parameters that are associated with the specified blood processing procedure; upon inputting into the controller an identification of the parameters that are to populate the display screen during performance of the procedure selected from the initial list the parameters and indicating a format in which the selected parameters are to be presented on the display screen, creating a display for the specified blood processing procedure; displaying current values of the selected parameters in the selected format during performance of the specified procedure; saving an image of the display screen periodically during performance of the specified blood processing procedure; and transferring information from the saved images of the display screens to a procedure record form.

In a related aspect, the parameters displayed in the initial list comprise at least one of procedure estimates, intra-procedure variables, and procedure results. In addition, the format in which the selected parameters are to be presented on the display screen is indicated by assigning a different number to each selected parameter so that the selected parameters are presented in number order. The information to be provided for procedure estimates are selected to be displayed on a first display, the information to be provided for intra-procedure data are selected to be displayed on a second display, and the information to be provided for a procedure summary are selected to be displayed on a third display.

If the specified blood processing procedure is a red blood cell (RBC) exchange procedure, and the initial list of parameters includes one or more of procedure start time, procedure end time, procedure time, FCR (Fraction of Cells Remaining), end Hct (Hematocrit), starting Hct, depletion Hct, AC (AntiCoagulant) used, AC to patient, ACWB (AntiCoagulated Whole Blood) processed, WB processed, RBC RF (Return Fluid) to patient; saline RF to patient, albumin RF to patient, RF to patient, plasma returned, removed volume, fluid balance (mL), fluid balance (%), saline used, and saline to patient.

In a second aspect, an automated system for processing blood or blood products including a programmable controller with an interactive display screen for displaying information and receiving operator input. The controller is further configured to display on the screen an initial list of parameters that are entered into the programmable controller by the operator and measured and/or calculated by the system for a specified blood processing procedure; permit the operator to select from the initial list the parameters that are to populate the display screen during performance of the procedure; permit the operator to indicate a format in which the selected parameters are to be presented on the display screen; save the parameters that are entered into the programmable controller by the operator and measured and/or calculated by the system during performance of the procedure; and transfer the saved parameters to a procedure record form upon conclusion of the procedure.

In a related aspect, the programmable controller is further configured to permit indication of the order in which the selected parameters are to be presented on the display screen by assigning a different number to each selected parameter, and to present the selected parameters in number order. Further, the programmable controller is configured to include on the initial list parameters comprising at least one of procedure estimates, intra-procedure variables, and procedure results.

If the specified blood processing procedure is a red blood cell (RBC) exchange procedure, the programmable controller is configured so that, the initial list of parameters includes one or more of procedure start time, procedure end time, procedure time, FCR (Fraction of Cells Remaining), end Hct (Hematocrit), starting Hct, depletion Hct, AC (AntiCoagulant) used, AC to patient, ACWB (AntiCoagulated Whole Blood) processed, WB processed, RBC RF (Return Fluid) to patient; saline RF to patient, albumin RF to patient, RF to patient, plasma returned, removed volume, fluid balance (mL), fluid balance (%), saline used, and saline to patient.

BRIEF DESCRIPTION OF THE DRAWINGS

FIG. 5 is exemplary of an initial list of parameters and the order in which they may be presented on the display screen of the system for a red blood cell exchange procedure.

FIG. 6 is an example of a display screen based on the input made to the initial list of parameters in FIG. 5.

DETAILED DESCRIPTION

The embodiments disclosed herein are for the purpose of providing an exemplary description of the present subject matter. They are, however, only exemplary, and the present subject matter may be embodied in various forms. Therefore, specific details disclosed herein are not to be interpreted as limiting the subject matter as defined in the accompanying claims.

The present disclosure provides a system and method for customizing the displays shown on the screen at various times during the procedure. The operator is able to select the specific procedure parameters to be displayed, and also select the order in which the parameters are displayed, in order to, e.g., simplify the display by including only information that the operator requires and to match the order that is used in the procedure record forms or record databases.

For a particular device, or for each different procedure that can be performed with the device, a list is presented to the operator on the display screen of all the parameters that are used, measured or calculated by the system for performing a specific procedure. The operator may then select which parameters are to be displayed for each stage of the procedure (i.e., pre-procedure, intra-procedure and post procedure), and prioritize the order in which the selected parameters will be presented on the display screen. If the operator chooses not to customize the displays, then the displays pre-programmed into the controller will be used. Thus, greater control over the data to be displayed is given to the operator, thus allowing the operator to meet his or her particular needs or preferences.

Figure 1:
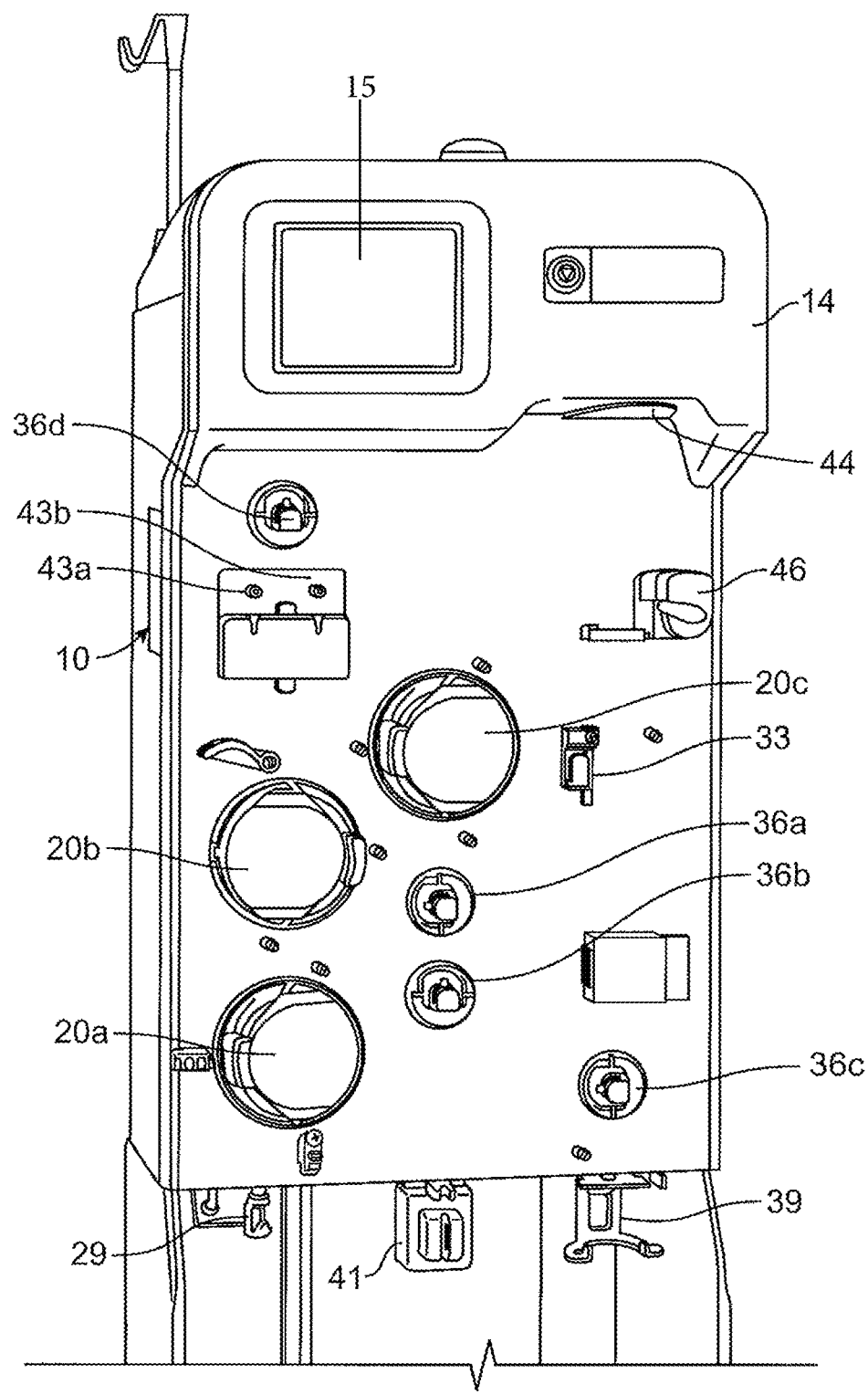
FIG. 1 is a front perspective view of an apheresis device in accordance with the present application.
Figure 2:
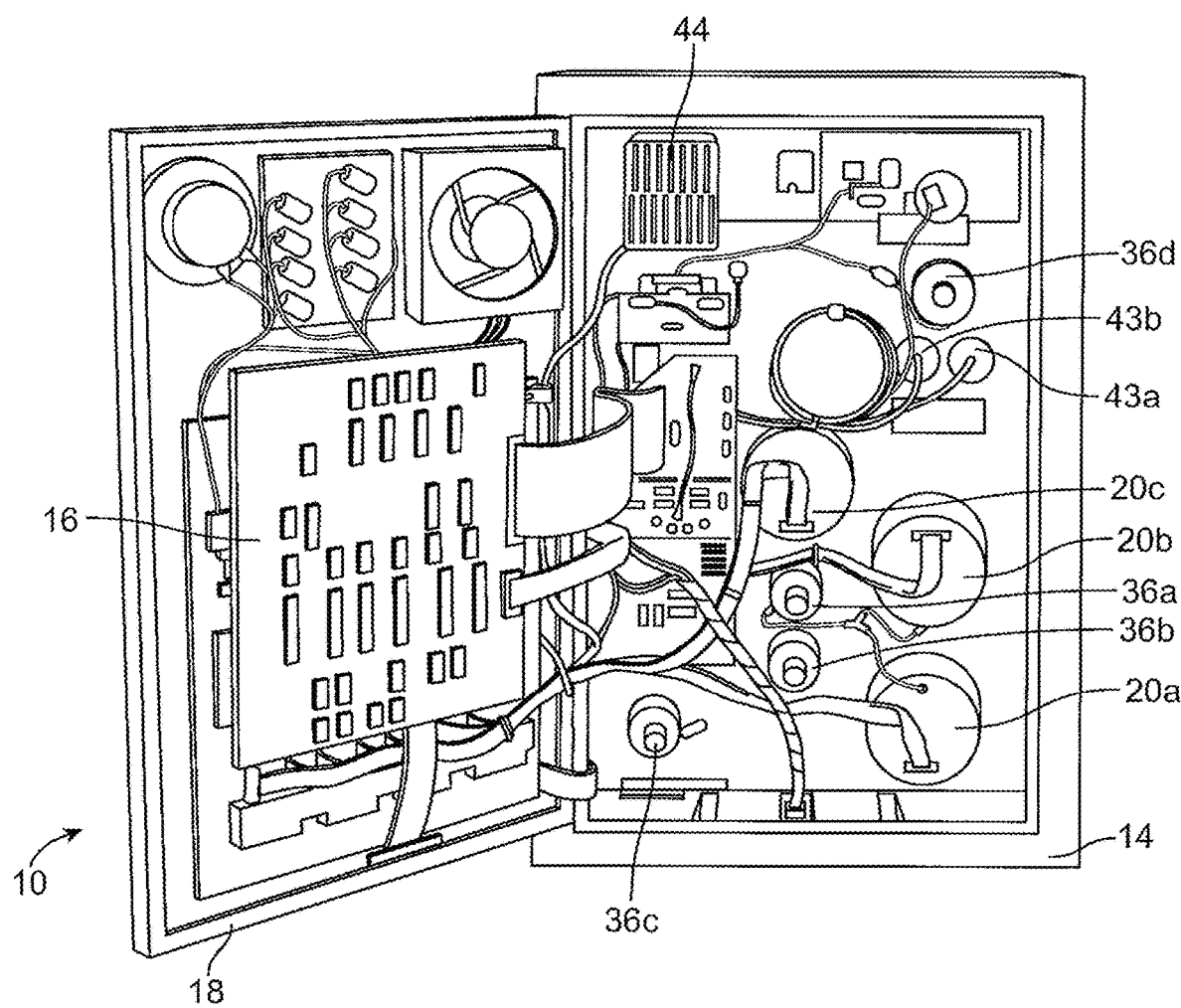
FIG. 2 is a rear perspective view of the apheresis device of FIG. 1, with a rear door thereof in an open position.
Figure 3:
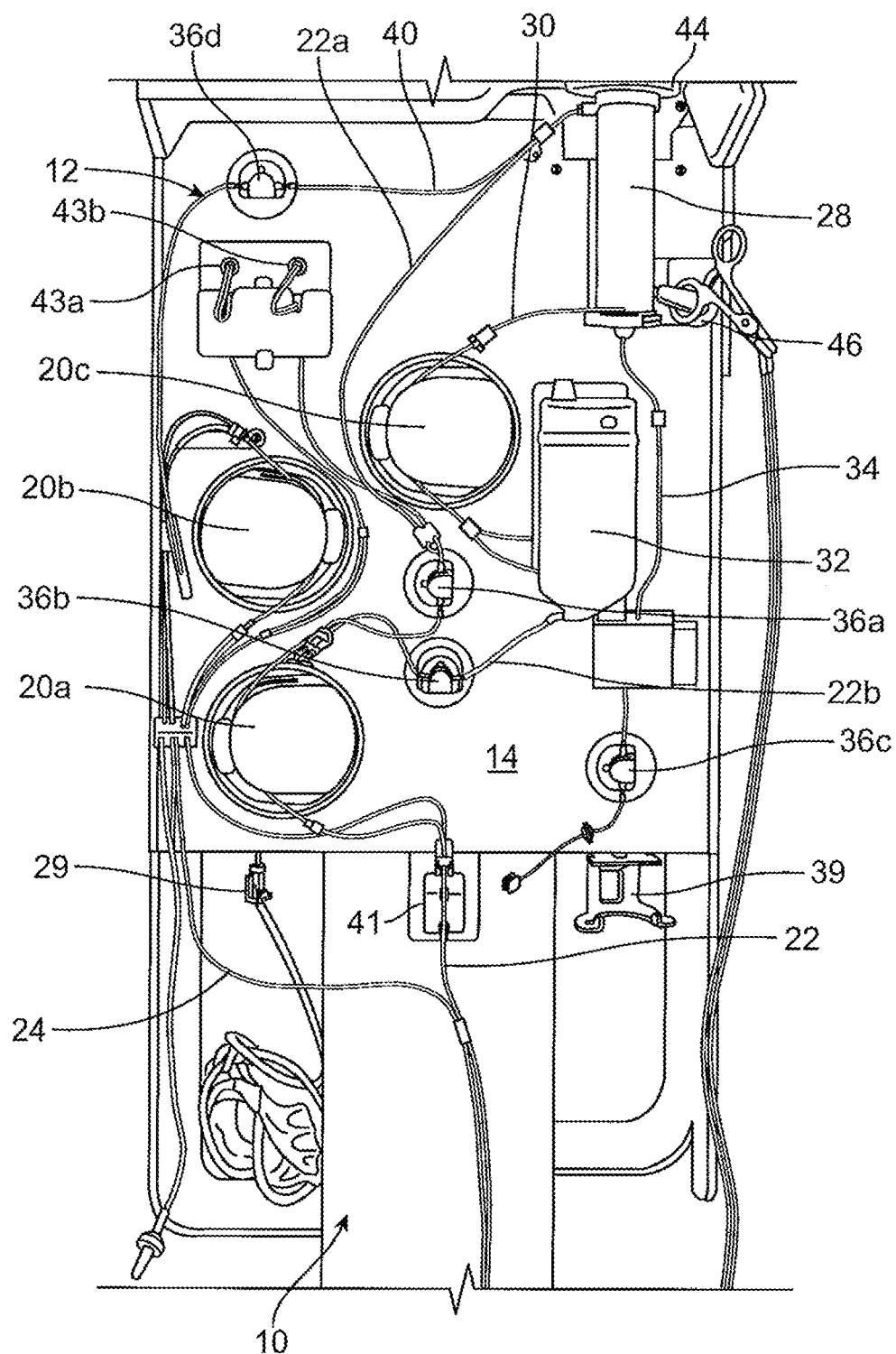
FIG. 3 is a front perspective view of the apheresis device of FIG. 1 with a fluid flow circuit associated therewith.

According to an aspect of the present disclosure, and as disclosed in US 2016/0175509, a durable or reusable fluid separation system is used in combination with a separate fluid flow circuit (which may be disposable) to separate a fluid into two or more constituent parts. FIGS. 1 and 2 illustrate an exemplary fluid separation system 10, while FIG. 3 illustrates an exemplary fluid flow circuit 12 mounted onto the fluid separation system 10.

The illustrated system 10 includes a cabinet or housing 14, with several components positioned outside of the cabinet 14 (e.g., associated with a front wall or surface or panel of the cabinet 14) and additional components (including a programmable central processing unit or controller 16) and interconnects positioned inside of the cabinet 14, which may be accessed by opening a rear door 18 of the system 10, as shown in FIG. 2. Among the system components positioned on the outside of the cabinet 14 is a touch screen 15 for inputting information into the controller 16 and displaying the input information or information originating from the controller. Additionally, one or more pumps or pump stations 20a-20c may be provided, with the pumps 20a-20c configured to accommodate tubing lines of the fluid flow circuit 12.

One of the pumps 20a may be provided as a source/recipient access pump, which may be associated with a source/recipient access line 22 of the fluid flow circuit 12 and operates to draw fluid from a fluid source (FIG. 5) during the draw or collection phase, operates in reverse to return fluid to a fluid recipient (FIG. 6) during a reinfusion stage, and is stopped at the end of the reinfusion phase. Pump 20a also primes the fluid flow circuit 12 and clears air from the access line 22. Pump 20a may also be referred to herein as a "blood pump," as it serves to pump whole blood from its source (such as a donor or, in the case of previously collected blood, a container or reservoir) to the separation module or chamber 28, described below.

A second pump 20b may be provided as an anticoagulant pump, which may be associated with an anticoagulant line 24 of the fluid flow circuit 12. Pump 22b thus operates to add anticoagulant from an anticoagulant source or container 26 of the fluid flow circuit 12 (FIG. 5) to fluid drawn from the fluid source in the source/recipient access line 22 before the fluid enters into a fluid separation module or chamber 28 of the fluid flow circuit 12. The anticoagulant container 26 is supported by a weigh scale hanger 29. Pump 20b does not, however, operate during the reinfusion phase of the procedure. Pump 20b may also be referred to herein as an "AC pump."

A third pump 20c may be provided as a return fluid pump, which may be associated with a return fluid outlet line 30 and operates to draw a return fluid (i.e., a fluid constituent to be returned to a fluid recipient) from the fluid separation chamber 28 and direct it into a return fluid reservoir 32 after the fluid has been separated into a return fluid and a collection fluid in the fluid separation chamber 28. The return fluid reservoir is supported by the weigh scale hanger 33. The pump 20c may also be used to prime the fluid flow circuit 12 and assist in clearing fluid from the fluid separation module 28 at the end of the procedure. Pump 20c does not, however, operate during the reinfusion phase of the procedure. Pump 20c may also be referred to herein as a "cell pump," as it serves to return cellular concentrate (i.e., concentrated red blood cells) to a donor in a plasmapheresis procedure.

In the illustrated embodiment, the pumps 20a-20c are peristaltic pumps, but diaphragm or other types of pumps could be provided. Furthermore, additional or alternative pumps may be provided without departing from the scope of the present disclosure. For example, a pump may be associated with a collection fluid outlet line 34 of the fluid flow circuit 12 to draw a collection fluid from the fluid separation chamber 28 after the fluid from the fluid source has been separated into a return fluid and a collection fluid. Also, as will be described in greater detail herein, the illustrated embodiment employs a single fluid flow tubing or flow path for both drawing fluid from a source and flowing or returning it to a recipient, which are carried out intermittently. The system 10 could employ separate draw and return flow paths or tubes without departing from the scope of the present disclosure.

In addition to the pumps 20a-20c, the external components of the system 10 may include one or more clamps or valves 36a-36d associated with the tubing lines of the fluid flow circuit 12. The clamps or valves 36a-36d may be variously configured and operate to selectively allow and prevent fluid flow through the associated tubing line. In the illustrated embodiment, one clamp or valve 36a may be provided as a fluid source/recipient clamp, which may be associated with a draw branch 22a of the source/recipient access line 22 of the fluid flow circuit 12 to allow or prevent the flow of fluid through the draw branch 22a of the source/recipient access line 22. Another one of the clamps or valves 36b may be provided as a reinfusion clamp or valve, which may be associated with a reinfusion branch 22b of the source/recipient access line 22 downstream of a return fluid reservoir 32 of the fluid flow circuit 12 to allow or prevent the flow of return fluid through the reinfusion branch 22b. A third clamp or valve 36c may be provided as a collection fluid clamp or valve, which may be associated with the collection fluid outlet line 34 to allow or prevent the flow of collection fluid through the collection fluid outlet line 34 and into a collection fluid container 38, which is supported by the weigh scale hanger 39. A fourth clamp or valve 36d may be provided as a replacement fluid clamp or valve, which may be associated with a replacement fluid line 40 of the fluid flow circuit 12 to allow or prevent the flow of a replacement fluid out of a replacement fluid source 42 (e.g., a bag or container at least partially filled with saline). Additional or alternative clamps or valves may also be provided without departing from the scope of the present disclosure.

The illustrated system 10 further includes one or more pressure sensors 43a and 43b that may be associated with the fluid flow circuit 12 to monitor the pressure within one or more of the tubing lines of the fluid flow circuit 12 during operation of the pumps 20a-20c and clamps or valves 36a-36d. In one embodiment, one pressure sensor 43a may be associated with a tubing line that draws fluid from a fluid source and/or directs processed fluid to a fluid recipient, while the other pressure sensor 43b may be associated with a tubing line that directs fluid into or out of the fluid separation chamber 28 to assess the pressure within the fluid separation chamber 28, but the pressure sensors 43a and 43b may also be associated with other tubing lines without departing from the scope of the present disclosure. The pressure sensors 43a and 43b may send signals to the system controller 16 that are indicative of the pressure within the tubing line or lines being monitored by the pressure sensor 43a, 43b. If the controller 16 determines that an improper pressure is present within the fluid flow circuit 12 (e.g., a high pressure due to an occlusion of one of the tubing lines), then the controller 16 may instruct one or more of the pumps 20a-20c and/or one or more of the clamps or valves 36a-36d to act so as to alleviate the improper pressure condition (e.g., by reversing the direction of operation of one of the pumps 20a-20c and/or opening or closing one of the clamps or valves 36a-36d). Additional or alternative pressure sensors may also be provided without departing from the scope of the present disclosure. In addition, the system 10 preferably includes an air detector 41 associated with the donor line 22 to provide a signal to the controller 16 when air is detected in the donor line.

The system 10 may also include a separation actuator 44 that interacts with a portion of the fluid separation chamber 28 to operate the fluid separation chamber 28. A chamber lock 46 may also be provided to hold the fluid separation chamber 28 in place with respect to the system cabinet 14 and in engagement with the separation actuator 44. The configuration and operation of the separation actuator 44 depends upon the configuration of the fluid separation chamber 28. In the illustrated embodiment, the fluid separation chamber 28 is provided as a spinning membrane-type separator, such as a separator of the type described in greater detail in U.S. Pat. Nos. 5,194,145 and 5,234,608 or in PCT Patent Application Publication No. WO 2012/125457 A1.

In the illustrated embodiment, the separation actuator 44 is provided as a driver that is magnetically coupled to the separation chamber 28 for causing the membrane of the separator rotate about the central axis of its housing.

Figure 4:
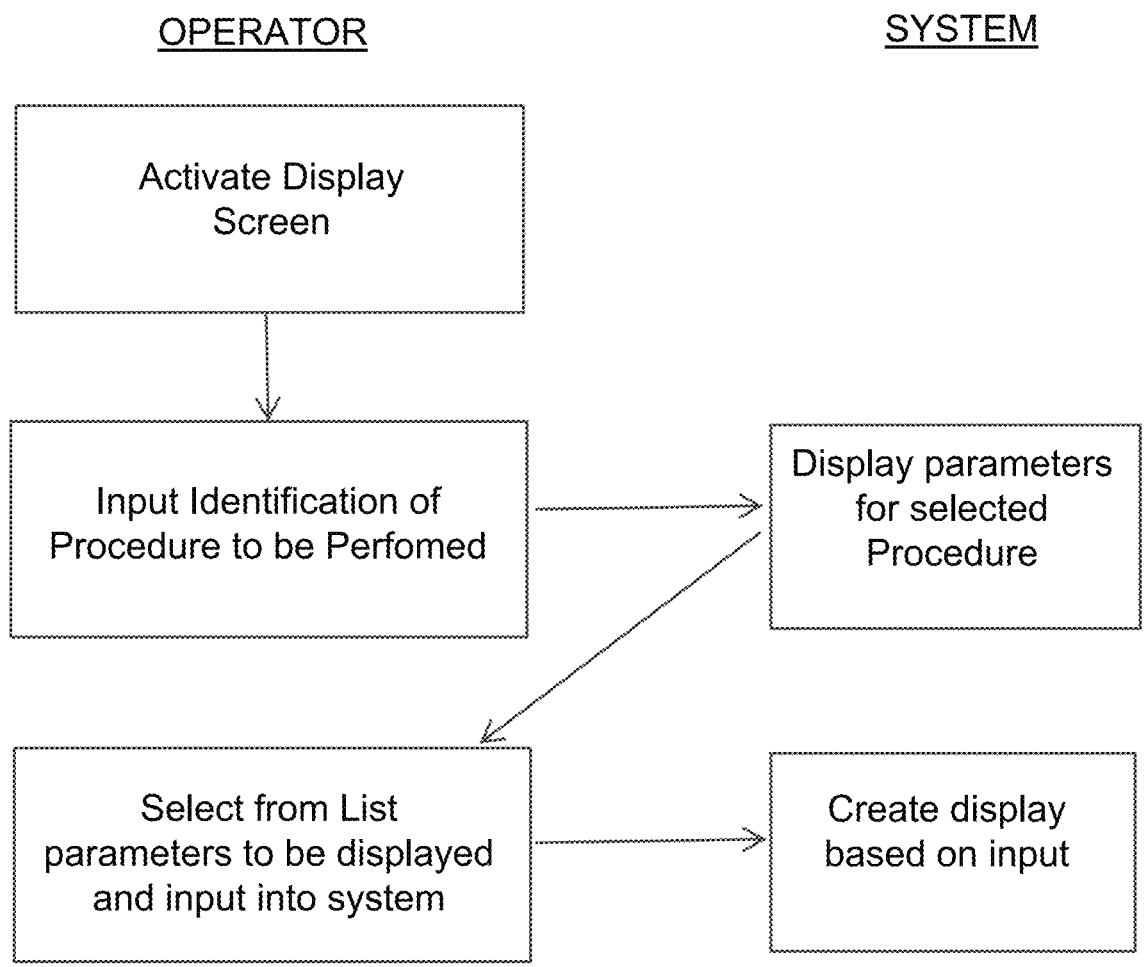
FIG. 4 is a flowchart illustrating the steps of the method

With reference to FIG. 4, a flow chart illustrating the steps of the method is seen. The operator will initially activate the display screen of the blood processing system. If the system is capable of performing more than one blood processing procedure, an identification of the specific procedure to be performed will be input into the controller, by, e.g., the operator indicating the procedure or by the controller automatically identifying the procedure by identifying a bar code or other information associated with the disposable flow circuit that is used for the procedure.

Upon the operator inputting into the controller an identification of the specific procedure to be performed, the control may also retrieve from a database and display an image of the procedure record form used by the operator's institution for the selected procedure to assist the operator in deciding which parameters are to be selected.

A comprehensive list of the parameters that are used, measured or calculated by the system for the selected procedure is then presented on the display screen. Preferably, the comprehensive list of parameters breaks down the parameters by the stage of the procedure to which they relate.

The operator then selects from the initial list and inputs into the controller those parameters that are to populate the display for each stage of the procedure. The operator indicates the order in which the selected parameters are to be displayed by, e.g., assigning a different number to each selected parameter and inputting the assigned number into the controller, so that the controller will display the selected parameters on the screen in number order.

As noted above, the listed parameters can be arranged according to the stage of the procedure to which they relate, i.e., pre-procedure, intra-procedure and post procedure, and a specific display screen can be created by the operator for each different stage.

By way of example, if the blood processing procedure to be performed is a red blood cell (RBC) exchange procedure, the initial list of parameters displayed on the screen, as shown in FIG. 4, may include one or more of: the procedure start time, procedure end time, procedure time, the fraction of cells remaining (FCR), the end hematocrit (Hct), the starting Hct, the depletion Hct, if anticoagulant (AC) is to be used, the total volume of AC to be used, the volume of AC to the patient, the volume of anticoagulated whole blood (ACWB) processed, the amount of WB processed, the volume of RBCs used as a return fluid (RF) to the patient, the amount of saline RF to the patient, the amount of albumin RF to the patient, the total volume of RF to the patient, the volume of plasma returned to the patient, the volume removed from the patient, the fluid balance (volume), the fluid balance (%), and, if saline is to be used, and the volume of saline to the patient.

The operator assigns consecutive numbers, starting with 1, to the parameters to indicate both whether the parameter is to be presented on the display and the order in which the parameters are to be listed. As seen in FIG. 5, fourteen parameters are selected and assigned numbers 1-14 to create a display of the procedure results shown in FIG. 6. In FIG. 6, the values associated with the selected parameters are representative of values that would result from a typical RBC exchange procedure, and are included only for illustrative purposes.

During the performance of the selected blood processing procedure, the current values of the selected parameters will be displayed on the screen in the selected format. Periodically during the performance of the selected procedure, an image of the display screen may be saved. The saved images may be retrieved at a later time for review.

Further, upon the completion of the selected procedure the information from the saved display screens may be transferred to a procedure record form. This may be done either by the operator inputting the required information into the procedure record form while reviewing the saved display screens, or the controller may automatically create the procedure record form based on the information on the saved screens that is displayed to the operator, and printed out and/or saved to the system database.

In keeping with another aspect of the disclosure, an automated system for processing blood or blood products is also provided that includes a programmable controller with an interactive display screen for displaying information and for receiving operator input. To this end, the controller is configured to permit an operator to select the information to be presented on the display screen.

More particularly, the controller is configured to display on the screen the initial list of parameters that are to be entered into the programmable controller by the operator and measured and/or calculated by the system for a specified blood processing procedure. The controller is further configured to permit the operator to select from the initial list the parameters that are to populate the display screen during the performance of the procedure and to further permit the operator to indicate the order in which the selected parameters are presented on the display screen.

In one embodiment, the controller is configured to permit the operator to assign a different number to each selected parameter indicative of the order in which the parameters are to be presented on the display screen.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope of the claims is not limited to the above description, but is set forth in the following claims.

The invention claimed is:

1. A method for processing blood or blood products using an automated system including a programmable controller, a database, and an interactive display screen for displaying information and receiving operator input, the method comprising:
   a) upon activation of the system, displaying on the screen a listing of different blood processing procedures that may be performed using the system;
   b) upon inputting into the controller an identification of a specified blood processing procedure that is to be performed, displaying on the screen an initial list of parameters that are associated with the specified blood processing procedure;
   c) upon inputting into the controller an identification of the parameters that are to populate the display screen during performance of the procedure selected from the initial list the parameters and indicating a format in which the selected parameters are to be presented on the display screen, creating a display for the specified blood processing procedure;
   d) displaying current values of the selected parameters in the selected format during performance of the specified procedure;
   e) saving an image of the display screen periodically during performance of the specified blood processing procedure; and
   f) transferring information from the saved images of the display screens to a procedure record form.

2. The method of claim 1 wherein the format in which the selected parameters are to be presented on the display screen is indicated by assigning a different number to each selected parameter so that the selected parameters are presented in number order.

3. The method of claim 1 wherein the parameters displayed in the initial list comprise at least one of procedure estimates, intra-procedure variables, and procedure results.

4. The method of claim 3 wherein the specified blood processing procedure is a red blood cell (RBC) exchange procedure, and the initial list of parameters includes one or more of procedure start time, procedure end time, procedure time, FCR (Fraction of Cells Remaining), end Hct (Hematocrit), starting Hct, depletion Hct, AC (AntiCoagulant) used, AC to patient, ACWB (AntiCoagulated Whole Blood) processed, WB processed, RBC RF (Return Fluid) to patient; saline RF to patient, albumin RF to patient, RF to patient, plasma returned, removed volume, fluid balance (mL), fluid balance (%), saline used, and saline to patient.

5. The method of claim 1 further comprising selecting the information to be provided for procedure estimates on a first display, for intra-procedure data on a second display, and for a procedure summary on a third display.

6. An automated system for processing blood or blood products including a programmable controller with an interactive display screen for displaying information and receiving operator input, the controller configured to:
   a) display on the screen an initial list of parameters that are entered into the programmable controller by the operator and measured and/or calculated by the system for a specified blood processing procedure;
   b) permit the operator to select from the initial list the parameters that are to populate the display screen during performance of the procedure;

c) permit the operator to indicate a format in which the selected parameters are to be presented on the display screen;
d) save the parameters that are entered into the programmable controller by the operator and measured and/or calculated by the system during performance of the procedure; and
e) transfer the saved parameters to a procedure record form upon conclusion of the procedure.

7. The automated system of claim 6 wherein the programmable controller is further configured to permit indication of the order in which the selected parameters are to be presented on the display screen by assigning a different number to each selected parameter, and to present the selected parameters in number order.

8. The automated system of claim 6 wherein the programmable controller is configured to include on the initial list parameters comprising at least one of procedure estimates, intra-procedure variables, and procedure results.

9. The automated system of claim 8 wherein the programmable controller is configured so that if the specified blood processing procedure is a red blood cell (RBC) exchange procedure, the initial list of parameters includes one or more of procedure start time, procedure end time, procedure time, FCR (Fraction of Cells Remaining), end Hct (Hematocrit), starting Hct, depletion Hct, AC (AntiCoagulant) used, AC to patient, ACWB (AntiCoagulated Whole Blood) processed, WB processed, RBC RF (Return Fluid) to patient; saline RF to patient, albumin RF to patient, RF to patient, plasma returned, removed volume, fluid balance (mL), fluid balance (%), saline used, and saline to patient.

10. The automated system of claim 6, wherein the controller is further configured to
display on the display screen a plurality of blood processing procedures that may be performed by the system before displaying the initial list of parameters, and
permit the operator to select the blood processing procedure to be performed by the system before displaying the initial list of parameters.

11. The automated system of claim 10, wherein the controller is further configured to display on the display screen an image of a procedure record form used by an institution of the operator after the operator has selected the blood processing procedure to be performed by the system.

12. The automated system of claim 6, wherein
the system is configured to perform a plurality of different blood processing procedures, and
the controller is configured to automatically identify the blood processing procedure to be performed by the system.

13. The automated system of claim 12, further comprising a bar code reader configured to detect a bar code of a fluid flow circuit to be used in combination with the system to perform the specified blood processing procedure, wherein the controller is configured to automatically identify the blood processing procedure to be performed by the system based on a bar code of a fluid flow circuit detected by the bar code reader.

14. The automated system of claim 6, wherein
the specified blood processing procedure comprises a plurality of stages, and
the initial list of parameters is broken down by the stage of the procedure to which each parameter relates.

15. The automated system of claim 6, wherein the controller is configured to display pre-programmed parameters on the display screen during performance of the procedure when the operator does not select the parameters to populate the display screen during performance of the procedure.

16. The automated system of claim 6, wherein the display screen is configured as a touch screen.

17. The automated system of claim 6, wherein the controller is further configured to save an image of the display screen during performance of the procedure.

18. The automated system of claim 17, wherein the controller is further configured to save a plurality of images of the display screen during performance of the procedure.

19. The automated system of claim 18, wherein the controller is further configured to automatically create the procedure record form based on said plurality of saved images of the display screen.

20. The automated system of claim 6, wherein the controller is further configured to permit the operator to select the parameters to be presented on the display screen before performance of the procedure, the parameters to be presented on the display screen during performance of the procedure, and the parameters to be presented on the display screen following performance of the procedure.

* * * * *